United States Patent
Whitehurst et al.

(10) Patent No.: US 6,788,975 B1
(45) Date of Patent: Sep. 7, 2004

(54) FULLY IMPLANTABLE MINIATURE NEUROSTIMULATOR FOR STIMULATION AS A THERAPY FOR EPILEPSY

(75) Inventors: Todd K. Whitehurst, Sherman Oaks, CA (US); James P. McGivern, Stevenson Ranch, CA (US); Janusz A. Kuzma, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 242 days.

(21) Appl. No.: 10/057,115

(22) Filed: Jan. 24, 2002

Related U.S. Application Data (60) Provisional application No. 60/265,008, filed on Jan. 30, 2001.

(51) Int. Cl.[7] ............................................... A61N 1/18
(52) U.S. Cl. ....................................................... 607/45
(58) Field of Search ........................... 607/45, 72, 115, 607/116, 118

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 5,193,539 A | 3/1993 | Schulman et al. | |
| 5,193,540 A | 3/1993 | Schulman et al. | |
| 5,215,086 A | 6/1993 | Terry, Jr. et al. | |
| 5,312,439 A | 5/1994 | Loeb | |
| 5,540,734 A | 7/1996 | Zabara | |
| 5,575,813 A * | 11/1996 | Edell et al. | 607/116 |
| 6,051,017 A | 4/2000 | Loeb et al. | |
| 6,161,044 A | 12/2000 | Silverstone | |
| 6,185,452 B1 | 2/2001 | Schulman et al. | |
| 6,205,359 B1 | 3/2001 | Boveja | |
| 6,405,079 B1 | 6/2002 | Ansarinia | |
| 6,415,184 B1 * | 7/2002 | Ishikawa et al. | 607/45 |
| 6,464,687 B1 | 10/2002 | Ishikawa et al. | |
| 6,526,318 B1 | 2/2003 | Ansarinia | |

FOREIGN PATENT DOCUMENTS

| | | |
|---|---|---|
| WO | WO-98/43700 A1 | 10/1998 |
| WO | WO-98/43701 A1 | 10/1998 |

OTHER PUBLICATIONS

Bazil, et al., "Advances in the Medical Treatment of Epilepsy", Annu. Rev. Med., vol. 49, (1998), pp. 135–162.

Beart, et al., "Excitatory Amino Acid Projections to the Nucleus of the Solitary Tract in the Rat: a Retrograde Transport Study Utilizing D–[3H]Aspartate and [3H]Gaba", J Auton Nerv Syst, vol. 50(1), (Dec. 1994), pp. 109–122.

Ben–Menachem, E., "Vagus Nerve Stimulation", Baillieres Clin Neurol, vol. 5(4), (Dec. 1996), pp. 841–848.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781–790.

Fanselow, et al., "Reduction of Pentylenetetrazole–Induced Seizure Activity in Awake Rats by Seizure–Triggered Trigeminal Nerve Stimulation", J Neurosci, vol. 20(21), (Nov. 2000), pp. 8160–8168.

(List continued on next page.)

Primary Examiner—Jeffrey R. Jastrzab
(74) Attorney, Agent, or Firm—Laura Haburay Bishop (57) ABSTRACT

A small implantable stimulator(s) with at least two electrodes is small enough to have the electrodes located adjacent to a nerve structure at least partially responsible for epileptic seizures. The small stimulator provides a means of stimulating a nerve structure(s) when desired, and may be implanted via a minimal surgical procedure.

3 Claims, 7 Drawing Sheets

OTHER PUBLICATIONS

Jeanmonod, et al., "Low–Threshold Calcium Spike Bursts in the Human Thalamus: Common Physiopathology for Sensory, Motor and Limbic Positive Symptoms", Brain, vol. 119, (1996), pp. 363–375.

Menetrey, et al., "Spinal and Trigeminal Projections to the Nucleus of the Solitary Tract: a Possible Substrate for Somatovisceral and Viscerovisceral Reflex Activation", J Comp Neurol, vol. 255(3), (Jan. 1987), pp. 439–450.

Nomura, et al., "Trigeminal Primary Afferent Neurons Projecting Directly to the Solitary Nucleus in the Cat: a transganglionic and Retrograde Horseradish Peroxidase Study", Neurosci Lett, vol. 50(1–3), (Sep. 1984), pp. 257–262.

Schreiber, et al., "Expression of Neuron–Specific Enolase in Adult Rat Brain Following Epilepticus", Exp Neurol, vol. 159(1), (Sep. 1999), pp. 329–331.

South, et al., "Substance P–Containing Trigeminal Sensory Neurons Project to the Nucleus of the Solitary Tract", Brain Res, vol. 372(2), (May 1986), pp. 283–289.

Van Laere, et al., "Vagus Nerve Stimulation Refractory Epilepsy: SPECT Activation Study", J Nucl Med, vol. 41(7), (Jul. 2000), pp. 1145–1154.

Velasco, et al., "Acute and Chronic Electrical Stimulation of the Centromedian Thalamic Nucleus: Modulation of Reticulo–Cortical Systems and Predictor Factors for Generalized Seizure Control", Arch Med Res, vol. 31(3), (May–Jun. 2000), pp. 305–315.

Walker, et al., "Regulation of Limbic Motor Seizures by GABA and Glutamate Transmission in Nucleus Tractus Solitarius", Epilepsia, vol. 40(8), (Aug. 1999), pp. 1051–1057.

* cited by examiner

FULLY IMPLANTABLE MINIATURE NEUROSTIMULATOR FOR STIMULATION AS A THERAPY FOR EPILEPSY

The present application claims the benefit of U.S. Provisional Patent Application Serial No. 60/265,008, filed Jan. 30, 2001, which application is incorporated herein by reference in its entirety.

FIELD OF THE INVENTION

The present invention generally relates to implantable stimulator systems, and more particularly relates to an implantable stimulator system utilizing one or more implantable microstimulators for treating epilepsy.

BACKGROUND OF THE INVENTION

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts 1–2% of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy; in Africa, AIDS and its related infections, malaria and meningitis, are common causes; in India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is therefore suspected that those who do experience such symptomatic seizures are more vulnerable for similar biochemical/neurotransmitter reasons.

BRIEF SUMMARY OF THE INVENTION

The invention disclosed and claimed herein provides means for chronically stimulating a trigeminal ganglion or ganglia, a trigeminal nerve(s), or branch(es) of a trigeminal nerve(s) with a miniature implantable neurostimulator that can be implanted with a minimal surgical procedure. This invention also provides means for chronically stimulating a greater occipital nerve(s), lesser occipital nerve(s), third occipital nerve(s), facial nerve(s), glossopharyngeal nerve(s), or a branch(es) of any of these neural structures with a miniature implantable neurostimulator that can be implanted with a minimal surgical procedure. Electrical stimulation of such targets may provide significant therapeutic benefit in the management of epilepsy.

To treat epilepsy, a miniature implantable neurostimulator, such as a Bionic Neuron (also referred to as a BION™ microstimulator) may be implanted via a minimal surgical procedure (e.g., injection or small incision) adjacent to a trigeminal ganglion or ganglia, trigeminal nerve(s), branch(es) of a trigeminal nerve(s) (e.g., ophthalmic nerve(s), maxillary nerve(s), and/or mandibular nerve(s)), or branch(es) of any of these neural structures. A BION may additionally or alternatively be implanted adjacent to a greater occipital nerve(s), a lesser occipital nerve(s), a third occipital nerve(s), a facial nerve(s), a glossopharyngeal nerve(s), or a branch(es) of any of these neural structures to treat epilepsy.

A microstimulator may be implanted via injection and/or via endoscopic means. A more complicated surgical procedure may be required for sufficient access to a particular nerve (e.g., a nerve surrounded by scar tissue) or for purposes of fixing the neurostimulator in place. A single microstimulator may be implanted, or two or more microstimulators may be implanted to achieve greater stimulation of one or more nerves.

The microstimulator used with the present invention possesses one or more of the following properties, among others:

- at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator; and
- a form factor making the microstimulator implantable via a minimal surgical procedure.

A microstimulator may operate independently, or in a coordinated manner with other implanted devices, or with external devices. For instance, a microstimulator may incorporate means for sensing epilepsy, which it may then use to control stimulation parameters in a closed loop manner. The sensing and stimulating means may be incorporated into a single microstimulator, or a sensing means may communicate sensed information to at least one microstimulator with stimulating means.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Recent studies in both developed and developing countries have shown that up to 70% of newly diagnosed children and adults with epilepsy can be successfully treated (i.e., complete control of seizures for several years) with antiepileptic drugs. After two to five years of successful treatment, drugs can be withdrawn in about 70% of children and 60% of adults without the patient experiencing relapses. However, up to 30% of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without devastating impacts on long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG to the left vagus nerve in the neck. Helix-shaped stimulation and indifferent electrodes are attached to the vagus nerve via an invasive surgical process that requires the carotid sheath to be fully exposed. Based on a number of studies, approximately 5% of patients undergoing VNS are seizure-free, and an additional 30–40% of patients have a greater than 50% reduction in seizure frequency.

In addition to this relatively low efficacy, VNS may lead to significant side effects. The vagus nerve provides parasympathetic innervation to the cardiac tissue, and thus VNS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of action of VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," Epilepsia, 1999 August) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. concludes that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nucleus) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in the cat, it was found that branches of the trigeminal nerve (the lingual and pterygopalatine nerves) were found to contain fibers which ended ipsilaterally in the rostral portions of the NTS, massively in the medial and ventrolateral NTS, moderately in the intermediate and interstitial NTS, and sparsely in the ventral NTS. (The rostral-most part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P-containing trigeminal sensory neurons project to the NTS.

There is also convincing evidence that a significant number of neurons in the trigeminal nucleus project to the NTS as well. In one study, retrograde transport of a protein-gold complex was used to examine the distribution of spinal cord and trigeminal nucleus caudalis neurons that project to the NTS in the rat. The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, it is suggested that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Another study utilized microinfusion and retrograde transport of D-[3H]-aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," Journal of Neuroscience, 2000 November) demonstrated that unilateral stimulation via a chronically implanted nerve cuff electrode applied to the infraorbital branch of the trigeminal nerve led to a reduction in electrographic seizure activity of up to 78%. The authors reported that bilateral trigeminal stimulation was even more effective.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3-Hz absence seizures and are believed to be involved in other types of epilepsy. Thalamic nuclei of some patients suffering from epilepsy display neuronal activities described as "low-threshold calcium spike bursts", which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

The "thalamic relay" theory has led researchers recently to begin implanting deep brain stimulation (DBS) systems for stimulation of either the centromedian nucleus or the anterior nucleus of the thalamus, in order to treat medically refractory epilepsy patients. Unfortunately, the efficacy of this invasive procedure has thus far proven to be approximately the same as VNS.

Drawbacks of VNS and DBS, such as size (of internal and/or external components), discomfort, inconvenience, and/or complex, risky, and expensive surgical procedures, has generally confined their use to patients with severe symptoms and the capacity to finance the surgery. Recently, an alternative to bulky implantable stimulation assemblies has been introduced. Small, implantable microstimulators can be injected into soft tissues through a cannula or needle. See, e.g., U.S. Pat. Nos. 5,324,316 and 5,405,367, both of which patents are incorporated herein by reference. Discussed herein are ways to effectively use such small, fully implantable, chronic neurostimulators for the purpose of treating epilepsy.

Figure 1A:
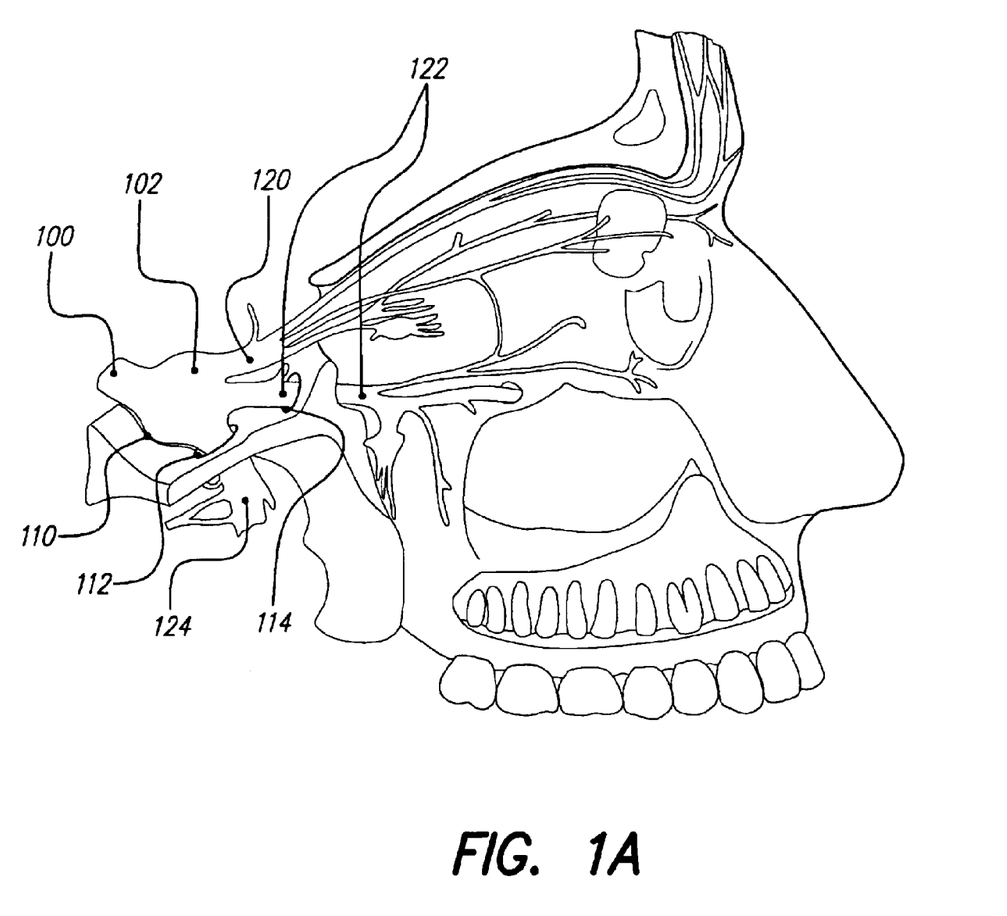
FIG. 1A depicts various nerve branches dorsal to the trigeminal nerve and nearby bony structures.
Figure 1B:
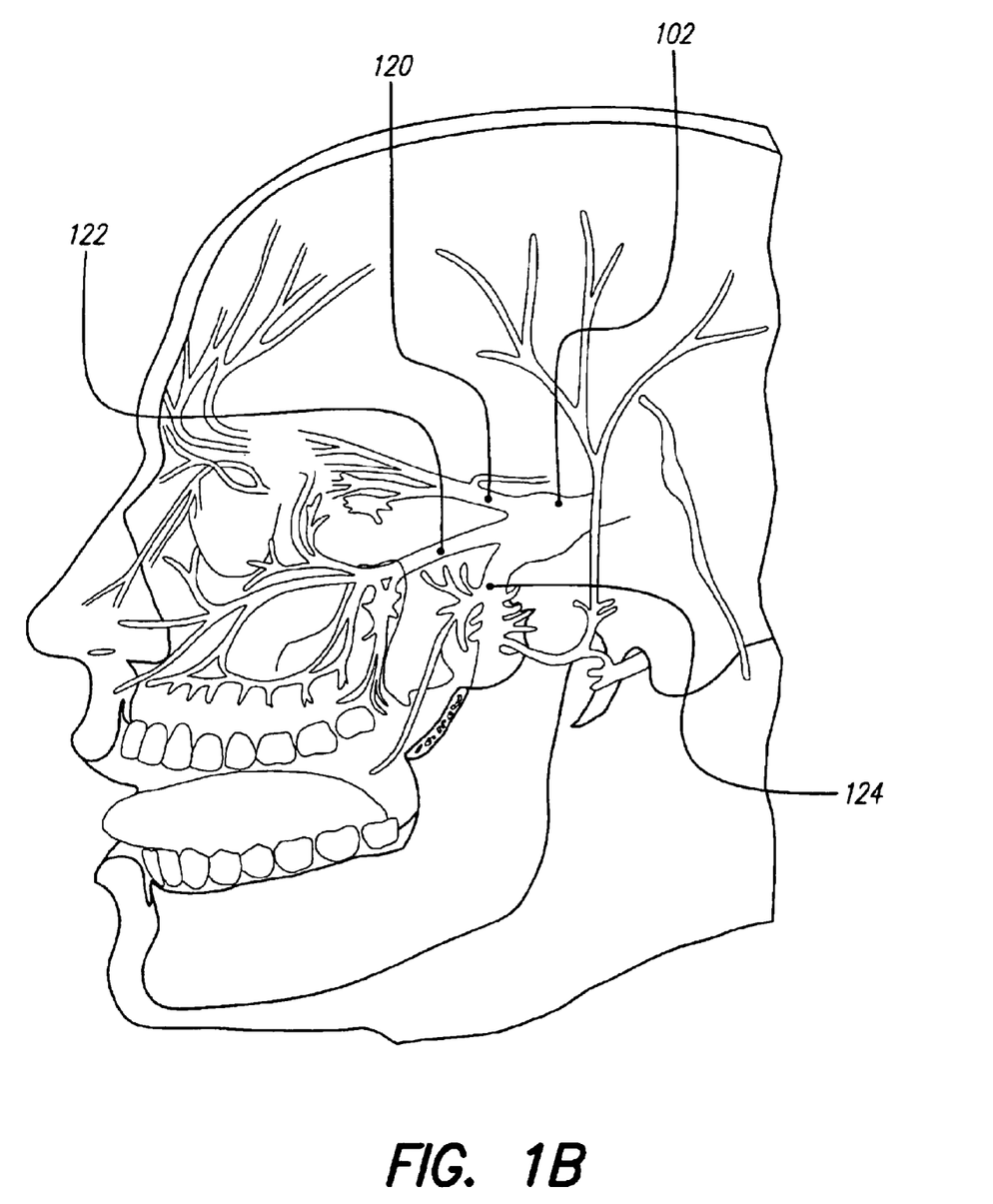
FIG. 1B illustrates the trigeminal nerve, and nerve branches dorsal and proximal to the trigeminal nerve.

FIGS. 1A and 1B depict the trigeminal nerve and its branches. The trigeminal nerve 100 on each side of the head arises from a trigeminal ganglion 102, which lies within the skull in an area known as Meckel's cave 110. In accordance with the teachings of the present invention, access to a trigeminal ganglion may be gained via the foramen ovale 112 or the foramen rotundum 114 in order to implant a miniature neurostimulator adjacent to one or both of the trigeminal ganglia 102.

Procedures that ablate the trigeminal ganglia 102 do not disable the muscles of mastication, since the cell bodies of the sensory portion of the nerve are within the trigeminal ganglion, whereas the motor portion simply projects axons through the ganglia (the motor neuron cell bodies are in the pons). This may provide a mechanism for selective stimulation of the sensory cells via appropriate placement of a microstimulator for stimulation of one or both trigeminal ganglia 102.

A miniature neurostimulator may additionally or alternatively be implanted adjacent to a trigeminal nerve 100 or any of its branches distal to one or both trigeminal ganglia 102, such as the ophthalmic nerve 120, the maxillary nerve 122, the mandibular nerve 124, and/or branch(es) of any of these. The ophthalmic nerve 120 and the maxillary nerve 122 are entirely sensory, and sufficiently separate to allow independent and selective stimulation via appropriate placement of a microstimulator.

The mandibular nerve 124 is both sensory and motor. The mandibular nerve 124 innervates several facial muscles, including the muscles of mastication and the tensor tympani, which reflexively damps down the vibrations of the malleus by making the tympanic membrane more tense. However, just distal to the foramen ovale 112, the mandibular nerve 124 splits into a purely sensory branch that innervates the superior part of the lower jaw. And slightly more distally, another branch splits into a purely sensory branch that innervates the inferior part of the lower jaw. These branches may be sufficiently separate to allow independent and selective stimulation via appropriate placement of a microstimulator.

Figure 2A:
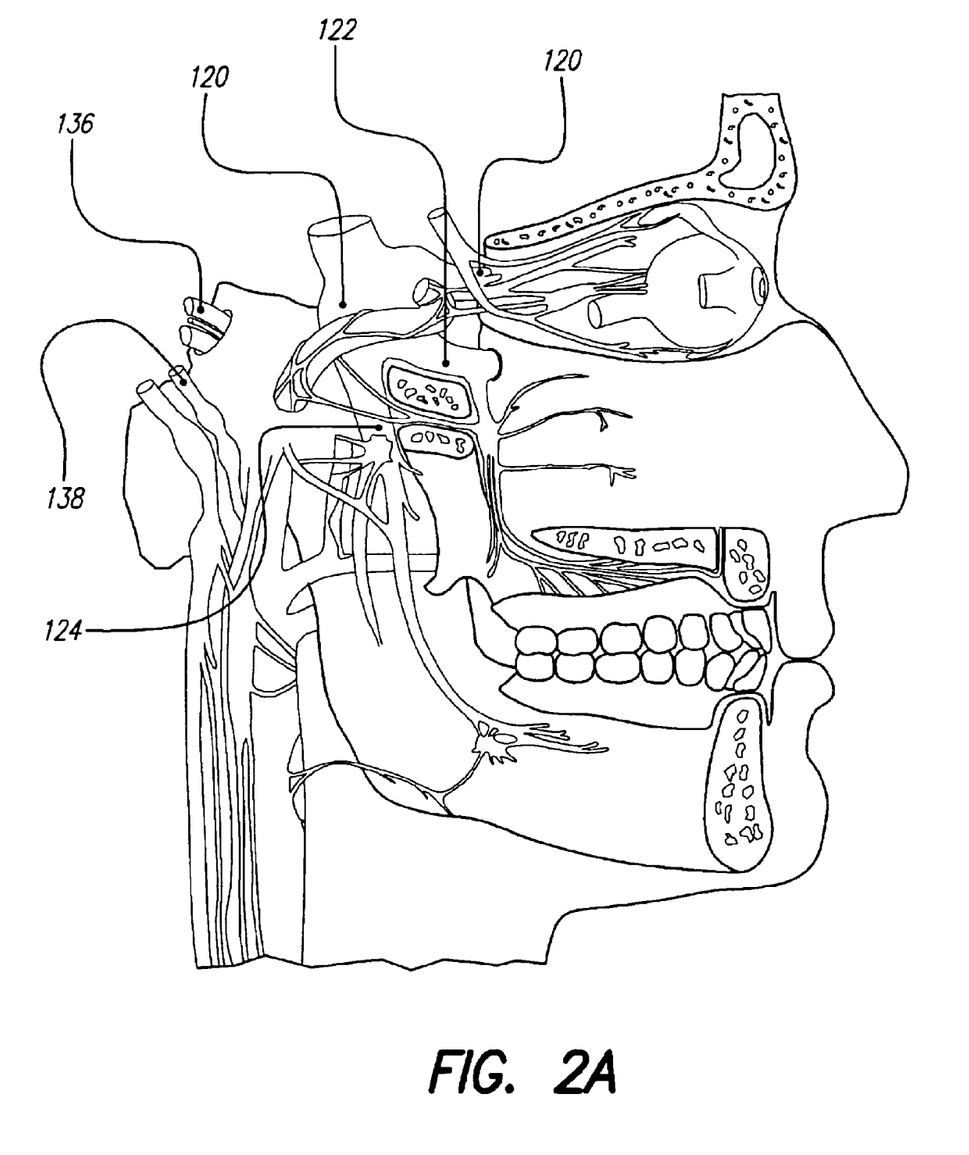
FIG. 2A illustrates various autonomic nerves in the head.
Figure 2B:
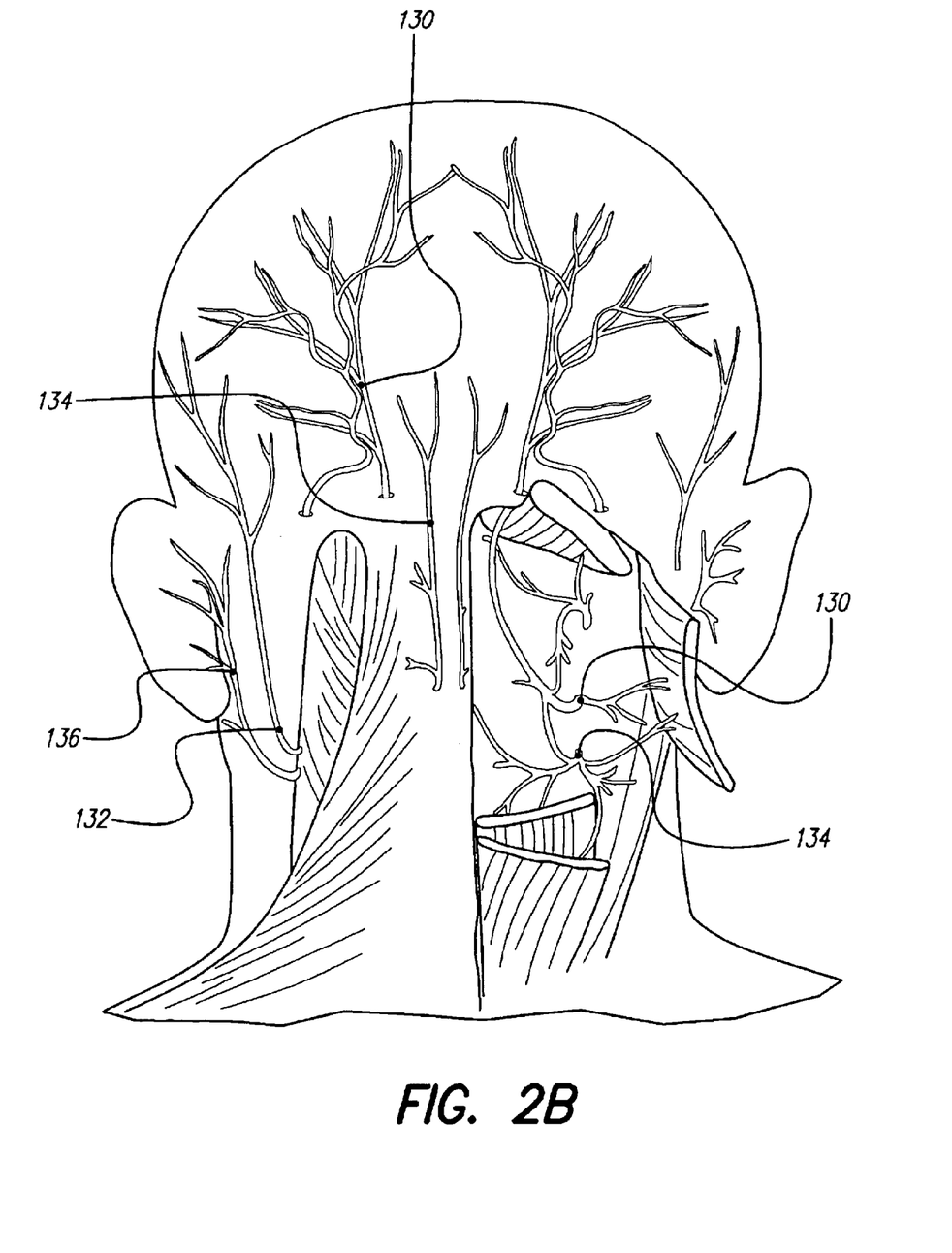
FIG. 2B depicts various nerves and muscles of the back of the head and neck.

Epilepsy may also be relieved with stimulation additionally or alternatively applied to the greater occipital nerve 130, the lesser occipital nerve 132, and/or the third occipital nerve 134, as well as the facial nerve(s) 136, glossopharyngeal nerve(s) 138, and/or branches of any of these (see FIGS. 2A and 2B). As seen in FIG. 2B, the occipital nerves are relatively easily accessed, especially in their distal portions, since they lie subcutaneously in the back of the head and upper neck.

In accordance with the teachings of the present invention, electrical stimulation at one or more of the above-mentioned and/or other trigeminal nerve branches is provided to relieve epilepsy. A microstimulator may be relatively easily implanted via injection and/or via endoscopic means adjacent to one or more of the above-identified nerves or nerve structures. A more complicated surgical procedure may be required for sufficient access to one or more of these nerve structures and/or for fixing the neurostimulator in place. The sites of injection or skin incision could be selected such that the scars would likely be covered by hair in most people.

As mentioned above, vagus nerve stimulation (VNS) has demonstrated limited efficacy in the treatment of patients with medically refractory epilepsy. As stated, the mechanism of action of VNS has not been confirmed, but a number researchers believe that VNS may exert its seizure reduction effects through afferent stimulation of the nucleus of tractus solitarius (NTS).

As detailed above, studies have shown that the trigeminal nerve also contributes a significant number of afferent fibers to the NTS. Additionally, trigeminal nerve afferents synapse on the trigeminal nucleus in the brainstem, and afferents from the trigeminal nucleus also project to the NTS. Thus, electrical stimulation of, for example, a trigeminal ganglion, trigeminal nerve, or branch(es) of the trigeminal nerve may reasonably be expected to demonstrate efficacy in the treatment of patients with medically refractory epilepsy.

Advantageously, stimulation of the trigeminal nerve does not pose the cardiac or vocal cord risks that are associated with VNS. The trigeminal nerve provides sensory innervation to the face, so stimulation may produce a tingling sensation. However, this feeling has not been reported to be unpleasant in patients undergoing sensory nerve stimulation, and in time, patients grow accustomed to the sensation. The trigeminal nerve also innervates the muscles of mastication, so excessive stimulation of these branches may cause fatigue or even spasm of the mandible (i.e., lockjaw). Stimulation of branches that are distal to the motor fibers of the trigeminal nerve should allow these potential motor side effects to be avoided altogether.

The present invention is directed to treating epilepsy using one or more small, implantable neurostimulators, referred to herein as "microstimulators". The microstimulators of the present invention are preferably similar to or of the type referred to as BION™ devices. The following documents describe various features and details associated with the manufacture, operation and use of BION implantable microstimulators, and are all incorporated herein by reference:

| application/ patent/ Pub. No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued June 28, 1994 | Implantable Microstimulator |
| U.S. Pat. No. 5,405,367 | Issued Apr. 11, 1995 | Structure and Method of Manufacture of an Implantable Microstimulator |
| U.S. Pat. No. 6,051,017 | Issued Apr. 18, 2000 | Improved Implantable Microstimulator and Systems Employing Same |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| | published September, 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 3:
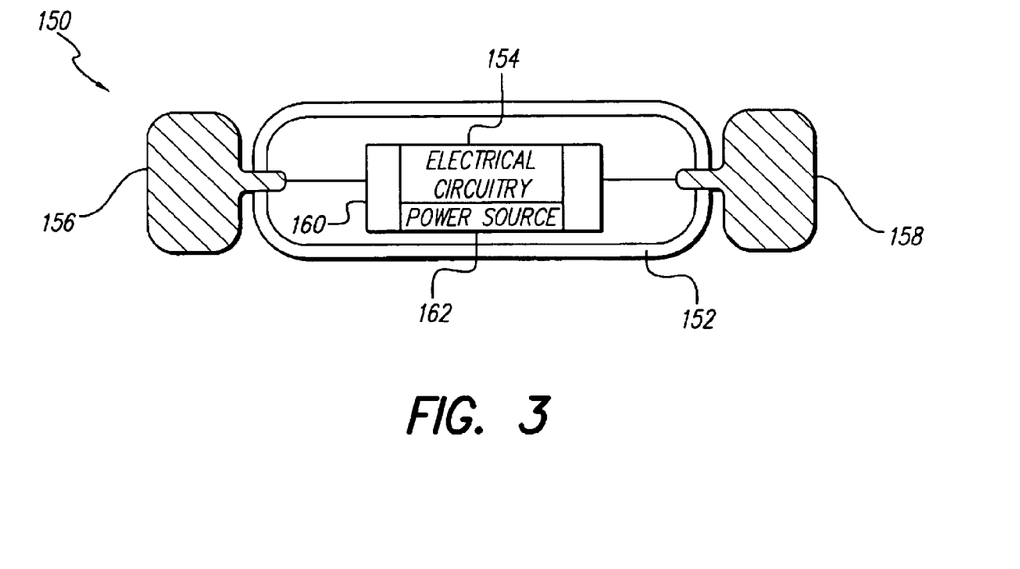
FIG. 3 illustrates an exemplary embodiment of a stimulation system of the present invention.

As shown in FIG. 3, microstimulator device 150 includes a narrow, elongated capsule 152 containing electronic circuitry 154 connected to electrodes 156 and 158, which may pass through the walls of the capsule at either end. As detailed in the referenced patent publications, electrodes 156 and 158 generally comprise a stimulating electrode (to be placed close to the nerve) and an indifferent electrode (for completing the circuit). Other configurations of microstimulator device 150 are possible, as is evident from the above-referenced patent publications, and as described in more detail herein.

Certain configurations of implantable microstimulator 150 are sufficiently small to permit its placement adjacent to the structures to be stimulated. (As used herein, "adjacent" and "near" mean as close as reasonably possible to targeted tissue, including touching or even being positioned within the tissue, but in general, may be as far as about 150 mm from the target tissue. A single microstimulator 150 may be implanted, or two or more microstimulators may be implanted to achieve greater stimulation of the targeted issue, or for a longer period of time.

Capsule 152 of FIG. 3 may have a diameter of about 4–5 mm, or only about 3 mm, or even less than about 3 mm. Capsule 152 length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3, is one possible configuration, but other shapes, such as spheres, disks, or helical structures, are possible, as are additional electrodes.

Microstimulator 150 may be implanted with a surgical insertion tool specially designed for the purpose, or may be injected (e.g., via a hypodermic needle). Alternatively, device 150 may be implanted via conventional surgical methods, or may be inserted using other endoscopic or laparoscopic techniques. A more complicated surgical procedure may be required for fixing the neurostimulator in place.

The external surfaces of stimulator 150 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and the device.

In certain embodiments of the instant invention, microstimulator 150 comprises two, leadless electrodes. However, either or both electrodes 156 and 158 may alternatively be located at the ends of short, flexible leads as described in U.S. patent application Ser. No. 09/624,130, filed Jul. 7, 2000, which is incorporated herein by reference in its entirety. The use of such leads permits, among other things, electrical stimulation to be directed more locally to targeted tissue(s) a short distance from the surgical fixation of the bulk of the implantable stimulator 150, while allowing most elements of stimulator 150 to be located in a more surgically convenient site. This minimizes the distance traversed and the surgical planes crossed by the device and any lead(s). In most uses of this invention, the leads are no longer than about 150 mm.

Microstimulator 150 contains, when necessary and/or desired, electronic circuitry 154 for receiving data and/or power from outside the body by inductive, radio-frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

Neurostimulator 150 includes, when necessary and/or desired, a programmable memory 160 for storing a set(s) of data, stimulation, and control parameters. Among other things, memory 160 may allow stimulation and control parameters to be adjusted to settings that are safe and efficacious with minimal discomfort for each individual. Specific parameters may provide therapeutic advantages for various forms of epilepsy. For instance, some patients may respond favorably to intermittent stimulation, while others may require continuous stimulation to alleviate their symptoms.

In addition, stimulation parameters may be chosen to target specific neural populations and to exclude others, or to increase neural activity in specific neural populations and to decrease neural activity in others. For example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity.

Some embodiments of implantable stimulator 150 also includes a power source and/or power storage device 162. Possible power options for a stimulation device of the present invention, described in more detail below, include but are not limited to an external power source coupled to stimulator 150, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

According to certain embodiments of the invention, a microstimulator operates independently. According to various embodiments of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, an optical link, or the like. Specifically, a microstimulator may communicate with an external remote control (e.g., patient and/or physician programmer) that is capable of sending commands and/or data to a microstimulator and that may also be capable of receiving commands and/or data from a microstimulator.

Figure 4:
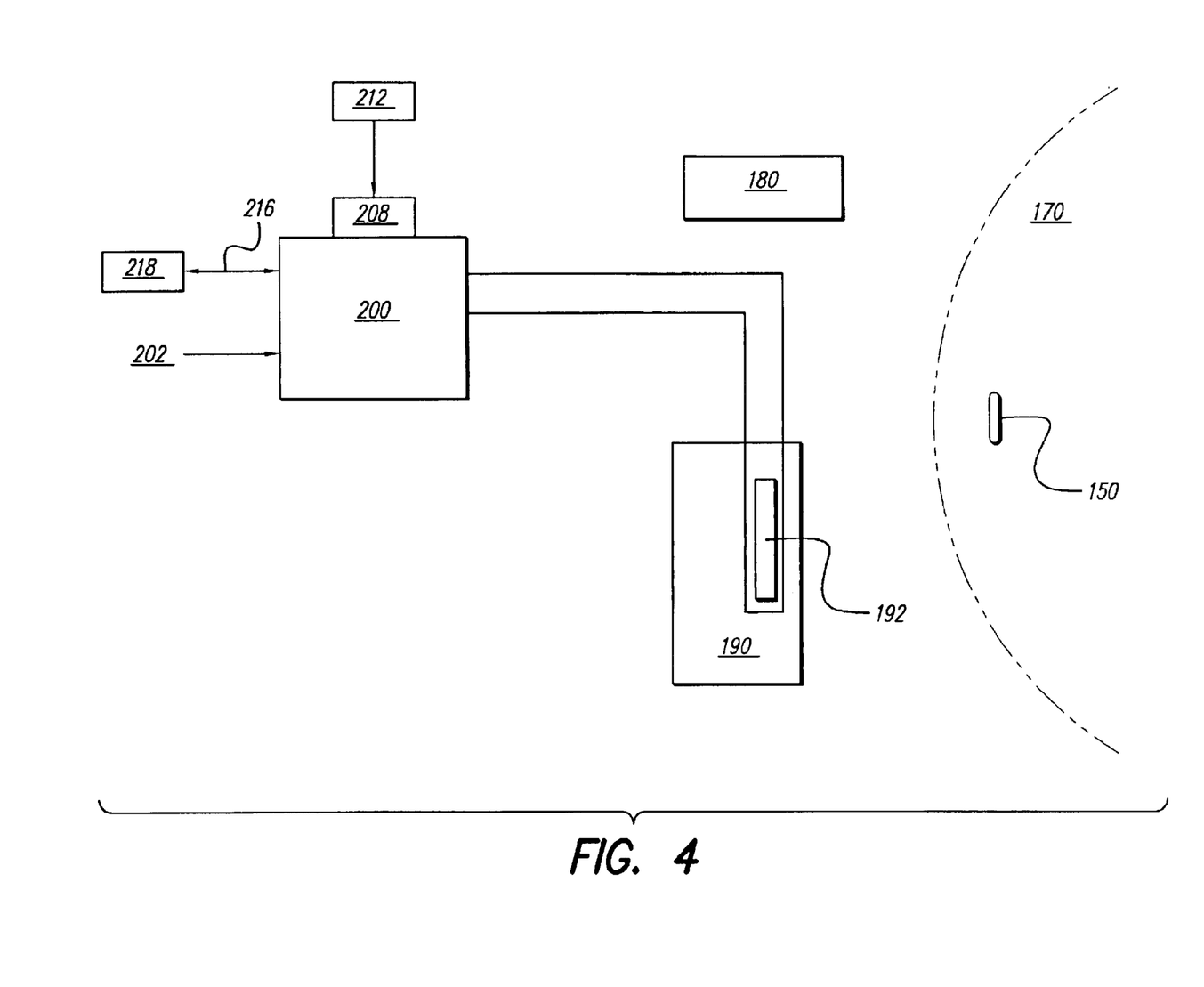
FIG. 4 illustrates preferred external components of the invention.

In certain embodiments, and as illustrated in FIG. 4, the patient 170 switches the implantable stimulator 150 on and off by use of controller 180, which may be handheld. Implantable stimulator 150 is operated by controller 180 by any of various means, including sensing the proximity of a permanent magnet located in controller 180, sensing RF transmissions from controller 180, or the like.

External components for programming and/or providing power to various embodiments of implantable stimulator 150 are also illustrated in FIG. 4. When communication with the implanted stimulator 150 is desired, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input means 208, e.g., a keypad, whereby the patient 170 or a caregiver 212 can request changes in the stimulation parameters produced during the normal operation of the implantable stimulator 150. In these embodiments, manual input means 208 includes various electromechanical switches and/or visual display devices that provide the patient and/or caregiver with information about the status and prior programming of the implantable stimulator 150.

Alternatively or additionally, external electronic appliance 200 is provided with an electronic interface means 216 for interacting with other computing means 218, such as by a serial interface cable or infrared link to a personal computer or to a telephone modem or the like. Such interface means 216 may permit a clinician to monitor the status of the implant and prescribe new stimulation parameters from a remote location.

The external appliance(s) may be embedded in a cushion, pillow, hat, or garment. Other possibilities exist, including a headband, patch or other structure(s) that may be affixed to the patient's body or clothing. External appliances may include a package that can be, e.g., worn on the belt, may include an extension to a transmission coil affixed, e.g., with a velcro band or adhesive, or may be combinations of these or other structures able to perform the functions described herein.

In order to help determine the strength and/or duration of electrical stimulation required to produce the desired effect, in some embodiments, a patient's response to and/or need for treatment is sensed. For example, electrical activity of the brain (e.g., EEG), electrical activity of a nerve (e.g., ENG), muscle activity (e.g., EMG), and/or abnormal movements resulting from a seizure (e.g., accelerometer activity) may be sensed. Other measures of the state of the patient may additionally or alternatively be sensed. For instance, medication, neurotransmitter, hormone, cytokine, and/or enzyme levels or their changes, and/or levels or changes in other substance(s) borne in the blood and/or in the cerebrospinal fluid (CSF) may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For instance, the level or changes in level of neuron-specific enolase, a key glycolytic enzyme, in either or both the blood serum or CSF may be sensed.

For example, when electrodes of implantable stimulator 150 are implanted adjacent to a trigeminal nerve branch, a sensor or stimulating electrode (or other electrode) of microstimulator 150 may be used to sense changes in EEG resulting from the stimulation applied to the nerve. Alternatively, a "microstimulator" dedicated to sensory processes communicates with a microstimulator that provides the stimulation pulses. The implant circuitry 154 may, if necessary, amplify and transmit these sensed signals, which may be analog or digital. Other methods of determining the required stimulation include a sensor implanted In the brain in an area where altered activity correlates with possible seizures (e.g., the seizure focus and/or near thalamic relay neurons), as well as other methods mentioned herein, and yet others that will be evident to those of skill in the art upon review of the present disclosure. The sensed information may be used to control stimulation parameters in a closed-loop manner.

For instance, in several embodiments of the present invention, a first and second "stimulator" are provided. The second "stimulator" periodically (e.g. once per minute) records a level of brain activity (or accelerometer activity, etc.), which it transmits to the first stimulator. The first stimulator uses the sensed information to adjust stimulation parameters according to an algorithm programmed, e.g., by a physician. For example, the amplitude of stimulation may be increased in response to increased activity in brain areas which demonstrate increased activity during epileptic attacks. In some alternatives, one stimulator performs both the sensing and stimulating functions, as discussed in more detail presently.

While a microstimulator may also incorporate means of sensing epileptic seizures, it may alternatively or additionally be desirable to use a separate or specialized implantable device to record and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with microstimulator 150, and may be used to accomplish, potentially among other things, one or more of the following functions:

Function 1: If necessary, transmit electrical power from the external electronic appliance 200 via appliance 190 to the implantable stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) used by stimulator 150.

Function 3: Transmit sensed data indicating a need for treatment or in response to stimulation from neurostimulator 150 (e.g., EEG, change in neurotransmitter or medication level, or other activity) to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for epilepsy may be carried out according to the following sequence of procedures:

1. A stimulator 150 is implanted so that its electrodes 156 and 158 are adjacent to a branch of trigeminal nerve 100. If necessary or desired, one or more additional stimulator(s) 150 may additionally or alternatively be implanted adjacent to other nerve structures, such as a trigeminal ganglion 102, ophthalmic nerve 120, maxillary nerve 122, mandibular nerve 124, greater occipital nerve 130, lesser occipital nerve 132, third occipital nerve 134, facial nerve 136, glossopharyngeal nerve 138, and/or branches of any of these nerves.

2. Using Function 2 described above (i.e., transmitting data) of external electronic appliance 200 and external appliance 190, implantable stimulator 150 is commanded to produce a series of electrical stimulation pulses with gradually increasing amplitude.

3. After each stimulation pulse, series of pulses, or at some other predefined interval, any change in, e.g., EEG and/or neurotransmitter and/or medication level is sensed, for instance, by one or more electrodes 156 and 158 or sensors (e.g., a CHEMFET). These responses are converted to data and telemetered out to external electronic appliance 200 via Function 3.

4. From the response data received at external appliance 200 from the implantable stimulator 150, or from other assessment, the stimulus threshold for obtaining a response is determined and is used by a clinician acting directly 212 or by other computing means 218 to transmit the desired stimulation parameters to the implantable stimulator 150 in accordance with Function 2.

5. When patient 170 desires to invoke electrical stimulation to alleviate symptoms, patient 170 employs controller 180 to set the implantable stimulator 150 in a state where it delivers a prescribed stimulation pattern from a predetermined range of allowable stimulation patterns.

6. To cease electrical stimulation, patient 170 employs controller 180 to turn off stimulator 150.

7. Periodically, the patient or caregiver recharges the power source/storage device 162 of implantable stimulator 150, if necessary, in accordance with Function 1 described above (i.e., transmit electrical power).

For the treatment of any of the various types and degrees of epilepsy, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 150, each of which could be separately controlled by means of a digital address. Multiple channels and/or multiple patterns of stimulation might thereby be programmed by the clinician and controlled by the patient in order to, for instance, stimulate larger areas of neural tissue in order to maximize therapeutic efficacy.

In some embodiments discussed earlier, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by microstimulator 150 are automatically adjusted based on the sensed information. Thus, the stimulation parameters are adjusted in a closed-loop manner to provide stimulation tailored to the need for and/or response to stimulation.

For instance, in some embodiments of the present invention, a first and second "stimulator" are provided. The second "stimulator" periodically (e.g. once per minute) records e.g., EEG, neurotransmitter level, and/or medication level, which it transmits to the first stimulator. The first stimulator uses the sensed information to adjust stimulation parameters according to an algorithm programmed, e.g., by a clinician. For example, stimulation amplitude may be activated or increased in response to increased seizure activity on EEG, e.g., increased number of spikes per minute recorded on EEG. Alternatively, one "microstimulator" performs both the sensing and stimulating functions.

Figure 5:
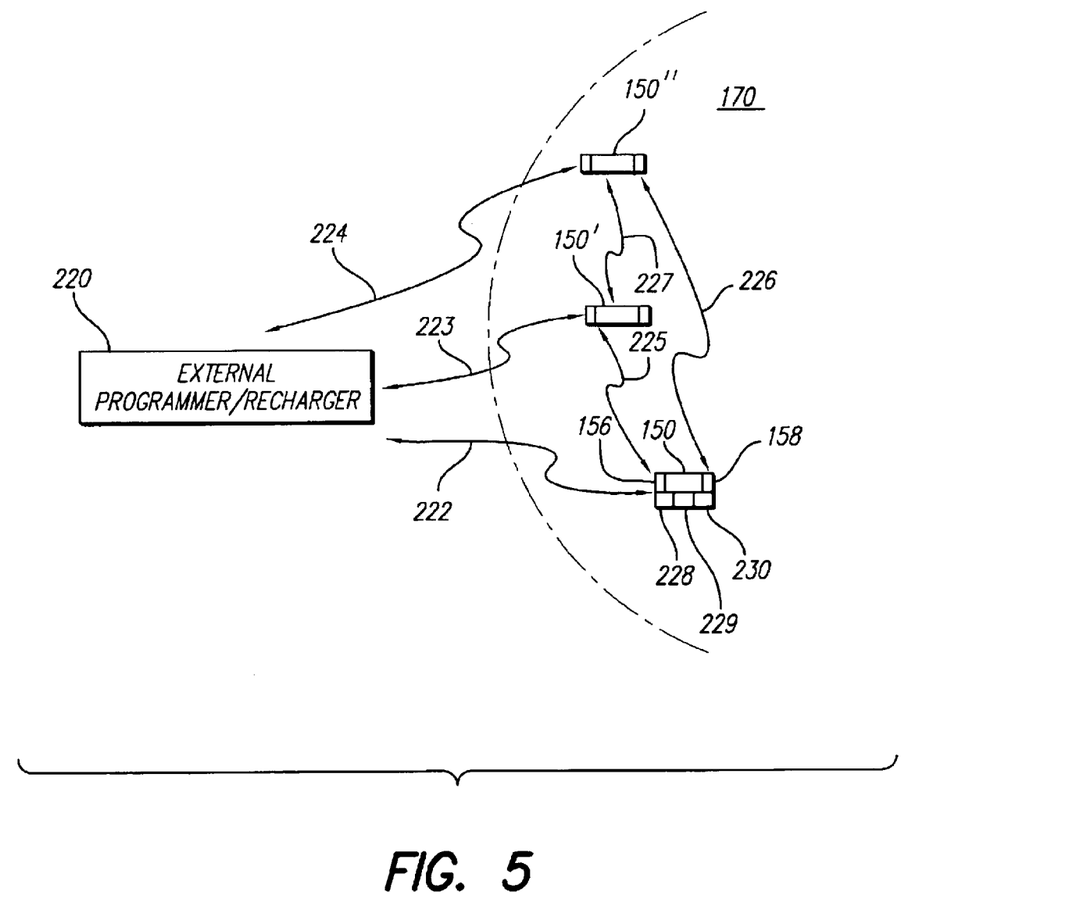
FIG. 5 depicts a system of implantable devices that communicate with each other and/or with external control/programming devices.

For example, as shown in the example of FIG. 5, a first microstimulator 150, implanted beneath the skin of patient 170, provides electrical stimulation via electrodes 156 and 158 to a first location; a second microstimulator 150' provides electrical stimulation to a second location; and a third microstimulator 150" provides electrical stimulation to a third location. As mentioned earlier, the implanted devices may operate independently or may operate in a coordinated manner with other similar implanted devices, other implanted devices, or other devices external to the patient's body, as shown by the control lines 222, 223 and 224 in FIG. 5. That is, in accordance with certain embodiments of the invention, external controller 220 controls the operation of each of the implanted microstimulators 150, 150' and 150". According to various embodiments of the invention, an implanted device, e.g. microstimulator 150, may control or operate under the control of another implanted device(s), e.g., microstimulator 150' and/or microstimulator 150". That is, a device made in accordance with the invention may communicate with other implanted stimulators, other implanted devices, and/or devices external to a patient's body, e.g., via an RF link, an ultrasonic link, a thermal link, an optical link, or other communications link. Specifically, as illustrated in FIG. 5, microstimulator 150, 150', and/or 150", made in accordance with the invention, may communicate with an external remote control (e.g., patient and/or physician programmer 220) that is capable of sending commands and/or data to implanted devices and that may also be capable of receiving commands and/or data from implanted devices.

A microstimulator made in accordance with the invention may incorporate, in some embodiments, first sensing means 228 for sensing therapeutic effects, clinical variables, or other indicators of the state of the patient, such as EEG, ENG, EMG, abnormal movements, and/or other marker of the potential for seizure. The stimulator additionally or alternatively incorporates second means 229 for sensing levels or changes in one or more medications, neurotransmitters, hormones, cytokines, enzymes, and/or other substances in the blood plasma, in the cerebrospinal fluid, or in the local interstitial fluid. The stimulator additionally or alternatively incorporates third means 230 for sensing electrical current levels and/or waveforms supplied by another source of electrical energy. Sensed information may be used to control the parameters. of the stimulator(s) in a closed loop manner, as shown by control lines 225, 226, and 227. Thus, the sensing means may be incorporated into a device that also includes electrical stimulation means, or the sensing means (that may or may not have stimulating means) may communicate the sensed information to another device(s) with stimulating means.

While a microstimulator may also incorporate means of sensing the condition of a patent, e.g., via EEG, ENG, EMG, or accelerometer activity, it may alternatively or additionally be desirable to use a separate or specialized implantable device to sense and telemeter physiological conditions/responses in order to adjust stimulation parameters. This information may be transmitted to an external device, such as external appliance 220, or may be transmitted directly to implanted stimulator(s) 150. However, in some cases, it may not be necessary or desired to include a sensing function or device, in which case stimulation parameters may be determined and refined, for instance, by patient feedback.

Again, microstimulator(s) 150 may be implanted adjacent to one or more of a trigeminal nerve 100, trigeminal ganglion 102, ophthalmic nerve 120, maxillary nerve 122, mandibular nerve 124, greater occipital nerve 130, lesser occipital nerve 132, third occipital nerve 134, facial nerve 136, glossopharyngeal nerve 138, and/or one or more nerve branches of any of these. According to several embodiments of the invention, symptoms of epilepsy are alleviated by decreasing excitement of these nerve fibers. As indicated above, inhibition of the NTS leads to a decrease in epileptic symptoms in certain types of epilepsy. Relatively high-frequency electrical stimulation (e.g., greater than about 100–150 Hz) is likely to produce such inhibition.

According to various embodiments of the invention, symptoms of certain other types of epilepsy are alleviated by alternatively increasing excitement of certain of these nerve fibers. Relatively low-frequency electrical stimulation (e.g., less than about 100–150 Hz) is likely to produce such excitement.

Additionally, sensing means described earlier may be used to orchestrate first the activation of microstimulator(s) targeting one or more nerves in one area, and then, when appropriate, the microstimulator(s) targeting nerves in the same or another area, in order to control symptoms, for instance, by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with epilepsy, comprising the steps of:

providing at least one means for stimulating tissue;

implanting the at least one stimulating means adjacent to at least one nerve structure at least in part responsible for epileptic seizures;

providing operating power to the at least one stimulating means;

transmitting stimulation parameters to the at least one stimulating means using at least one external appliance;

receiving and storing the stimulation parameters;

generating stimulation pulses in accordance with the stimulation parameters; and delivering the stimulation pulses to nerves structures adjacent to the at least one stimulating means;

wherein the stimulating means has a size and shape suitable for placement near the at least one nerve and has leads up to 150 mm long.

2. The method of claim 1 wherein the body of the stimulator is no more than 150 mm from the at least one nerve structure to be stimulated.

3. The method of claim 2 wherein the at least one nerve structure comprises at least one of a trigeminal nerve, a branch of the trigeminal nerve, a trigeminal ganglion, an ophthalmic nerve, a branch of the ophthalmic nerve, a maxillary nerve, a branch of the maxillary nerve, a mandibular nerve, a branch of the mandibular nerve, a greater occipital nerve, a branch of the greater occipital nerve, a lesser occipital nerve, a branch of the lesser occipital nerve, a third occipital nerve, a branch of the third occipital nerve, a facial nerve, a branch of the facial nerve, a glossopharyngeal nerve, and a branch of the glossopharyngeal nerve.

* * * * *